US008301223B2

(12) United States Patent
Lee et al.

(10) Patent No.: US 8,301,223 B2
(45) Date of Patent: Oct. 30, 2012

(54) NEUROBIOLOGICAL METHOD FOR MEASURING HUMAN INTELLIGENCE AND SYSTEM FOR THE SAME (75) Inventors: Kun Ho Lee, Seoul (KR); Yu Yong Choi, Suwon (KR); Kyung Jin Kim, Seoul (KR); Jong Min Lee, Suwon-Si (KR)

(73) Assignee: SNU R&DB Foundation, Seoul (KR)

( * ) Notice: Subject to any disclaimer, the term of this patent is extended or adjusted under 35 U.S.C. 154(b) by 338 days.

(21) Appl. No.: 12/376,799

(22) PCT Filed: Aug. 9, 2007

(86) PCT No.: PCT/KR2007/003830
§ 371 (c)(1),
(2), (4) Date: Dec. 12, 2009

(87) PCT Pub. No.: WO2008/018763
PCT Pub. Date: Feb. 14, 2008

(65) Prior Publication Data
US 2010/0174171 A1 Jul. 8, 2010

Related U.S. Application Data (60) Provisional application No. 60/821,825, filed on Aug. 9, 2006.

(51) Int. Cl.
A61B 5/05 (2006.01)
(52) U.S. Cl. ........ 600/410; 600/407; 600/411; 600/413; 600/418; 324/300; 324/307; 324/312; 382/128
(58) Field of Classification Search .................. 600/407, 600/410, 411, 413, 418; 324/300, 307, 312; 382/100, 128, 155, 156, 157, 158, 159
See application file for complete search history.

(56) References Cited

U.S. PATENT DOCUMENTS

| 6,144,873 | A | 11/2000 | Madore et al. |
| 6,292,683 | B1 | 9/2001 | Gupta et al. |
| 6,702,757 | B2 | 3/2004 | Fukushima et al. |
| 6,708,053 | B1 * | 3/2004 | Brooks et al. ................. 600/410 |

OTHER PUBLICATIONS

"Structural brain variation and general intelligence" by R.J. Haier, R. E. Jung, R. A. Yeo, K. Head, and M.T. Alkire. NeuroImage. 23. pp. 425-433 (2004).*
"Functional MRI evidence for disparate developmental processes underlying intelligence in boys and girls" by V.J. Schmithorst and S.K. Holland. NeuroImage. 31. pp. 1366-1379 (2006).*

(Continued)

Primary Examiner — Tse Chen
Assistant Examiner — Jason Ip
(74) Attorney, Agent, or Firm — Edwards Wildman Palmer LLP (57) ABSTRACT A method for measuring human intelligence using a neurobiogical model is provided. The method enables neurometric IQ to be measured by processing MRI and fMRI images of a subject to determine cortical thicknesses and brain activation level, determining structural IQ (sIQ) and functional IQ (fIQ) from the determined cortical thicknesses and brain activation level, and using the structural IQ (sIQ) and the functional IQ (fIQ) as predictors to measure the neurometric IQ of the subject. With this, individual differences in general cognitive ability can be easily assessed. It suggests that general cognitive ability can be explained by two different neural bases or traits: facilitation of neural circuits and accumulation of crystallized knowledge.

2 Claims, 6 Drawing Sheets

OTHER PUBLICATIONS

"Neural correlates of intelligence as revealed by fMRI of fluid analogies" by J.G. Geake and P.C. Hansen. NeuroImage. 26, pp. 555-564, Mar. 2005.*

"Measuring the thickness of the human cerebral cortex from magnetic resonance images" by B. Fischl and A.M. Dale. PNAS. vol. 97, No. 20, pp. 11050-11055, 2000.*

"Assessment of Normal-Appearing White and Gray Matter in Patients with Primary Progressive Multiple Sclerosis" by M. Rovaris et al. Arch Neurol. vol. 59, pp. 1406-1412, 2002.*

International Search Report for PCT/KR2007/003830, mailed Nov. 14, 2007.

* cited by examiner

NEUROBIOLOGICAL METHOD FOR MEASURING HUMAN INTELLIGENCE AND SYSTEM FOR THE SAME

CROSS-REFERENCES TO RELATED APPLICATIONS

This application is a U.S. national phase application, pursuant to 35 U.S.C. §371, of PCT/KR2007/003830, filed Aug. 9, 2007, designating the United States and published on Feb. 14, 2008 as WO 2008/018763 A1, which claims priority to U.S. Application No. 60/821,825, filed Aug. 9, 2006. The entire contents of the aforementioned patent applications are incorporated herein by this reference.

TECHNICAL FIELD

The present invention relates to a method of measuring human intelligence using a neurobiological model.

BACKGROUND ART

General intelligence generally refers to intellectual ability, which is conceptually somewhat different from the general factor g or fluid reasoning ability. In the psychometric tradition, it is widely accepted that there are two related but distinct components of general intelligence, referred to as "fluid (gF) and crystallized (gC) general intelligence" (Cattell 1963; 1987, Theory of fluid and crystallized intelligence: A critical experiment. J. Educ. Psychol., 54, 1-22; Cattell, R. B. (1987). Intelligence: Its structure, growth and action. New York: Elsevier Science). gF generally refers to reasoning and novel problem-solving ability, to be able to see relationships, as in analogies and letter and number series, which is independent from prior experience and learned knowledge. In contrast, gC is cognitive functioning based on previously acquired knowledge available in long-term store, including semantic knowledge and episodic memory.

Since the early 20$^{th}$ century, many psychometric batteries (i.e., IQ tests; for example the Wechsler-derived batteries, the Thorndike test, the Kaufman test, the Raven test) have been devised to measure individual differences in general intelligence. Using the batteries, psychometricians have attempted to clarify sources of individual differences, ultimately in order to enhance the cognitive functions. However, the mechanisms still are unclear because psychometric researches provide the correlational evidence rather than the causal evidence (Neisser, U., Boodoo, G., Bouchard, T. J. J., Boykin, A. W., Brody, N., Ceci, S. J., et al. (1996). Intelligence: Knowns and unknowns. Am. Psychol., 51, 77-101).

The RAPM (Raven's Advanced Progressive Matrices Set II), a standard test for general intelligence, is one of the purest measures of psychometric g (Raven, J., Raven, J. C., & Court, J. H. (1998). Manual for Raven's Progressive Matrices and Vocabulary Scales. Oxford: Oxford Psychologists Press). The WAIS (Wechsler's Adult Intelligence Scale), a standard intelligence quotient (IQ) test, is a measure of both crystallized intelligence (gC) and fluid intelligence (gF) based on eleven subtests (Marshalek, B., Lohman, D. F., & Snow, R. (1983). The complexity continuum in the radex and hierarchical models of intelligence. Intelligence, 7, 107-127; Wechsler, D. (1981). WAIS-R Manual. New York: Psychol. Corp): Information, Comprehension, Vocabulary, Similarities, Block Design, Object Assembly, Picture Completion, Digit Span, Arithmetic, Digit Symbol, and Picture Arrangement. Factor analytical studies of WAIS found the presence of factors named Verbal Comprehension and Perceptual Organization, and demonstrated that Information, Comprehension, Vocabulary, and Similarities subtests are classified into strong measures of Verbal Comprehension or gC, and Block Design, Object Assembly, and Picture Completion subtests are categorized into strong measures of Perceptual Organization or gF (Beck, N. C., Horwitz, E., Seidenberg, M., Parker, J., & Frank, R. (1985). WAIS-R factor structure in psychiatric and general medical patients. J Consult Clin Psychol, 53(3), 402-405; Leckliter, I. N., Matarazzo, J. D., & Silverstein, A. B. (1986). A literature review of factor analytic studies of the WAIS-R. J Clin Psychol, 42(4), 332-342; Marshalek, B., Lohman, D. F., & Snow, R. (1983). The complexity continuum in the radex and hierarchical models of intelligence. Intelligence, 7, 107-127; McGrew, K. S., & Flanagan, D. P. (1998). The Intelligence Test Desk Reference (ITDR): Gf-Gc Cross-Battery Assessment. Boston: Allyn & Bacon; Parker, K. (1983). Factor analysis of the WAIS-R at nine age levels between 16 and 74 years. Journal of Consulting and Clinical Psychology, 51, 302-308).

Over the last decade, neuroimaging studies using various techniques including anatomical MRI (Magnetic Resonance Image), fMRI (functional MRI), PET (Positron Emission Tomography), and MRS (Magnetic Resonance Spectroscopy) rapidly have unveiled the neurobiological bases of diverse cognitive functions such as fluid reasoning, working memory, and problem-solving ability (Gray, J. R., & Thompson, P. M. (2004). Neurobiology of intelligence: science and ethics. Nat. Rev. Neurosci., 5, 471-482). However, this approach appears to have some intrinsic limitations to differentiate the neural basis of gC from gF or the unitary factor g. First, individual differences in gF and gC exhibit robust inter-correlation in the normal cohort (r=0.7-0.8, Jensen, A. R. (1998). The g factor: The science of mental ability. Westport, Conn.: Praeger; Kaufman, A. S., & Horn, J. L. (1996). Age changes on test of fluid and crystallized ability for women and men on the Kaufman adolescent and adult intelligence test (KAIT) at ages 17-94 years. Archives of Clinical Neuropsychology, 11, 97-121). Their relation could be explained by the notion that gF plays a substantial role in encoding and retrieving information in long-term store and thereby in facilitating the accumulation and expression of gC, although there are distinct neural bases for these two functional domains (gF and gC) of intelligence. Second, the typical crystallized knowledge content of WAIS (Wechsler's Adult Intelligence Scale) subtests Information and Vocabulary reveals high g-loadings (r=0.6-0.7) despite low reliance on fluid reasoning ability and working memory capacity (Colom, R., Jung, R. E., & Haier, R. J. (2006). Distributed brain sites for the g-factor of intelligence. NeuroImage, 31(3), 1359-1365; Lee, K. H., Choi, Y. Y., Gray, J. R., Cho, S. H., Chae, J. H., Lee, S., et al. (2006). Neural correlates of superior intelligence: stronger recruitment of posterior parietal cortex. NeuroImage, 29(2), 578-586).

Therefore, to dissect the neural mechanism specific for crystallized knowledge, more sophisticated experimental paradigms and methods are required.

The present inventors have formulated a combined model of gF and gC that accounts for dissociation of gC and gF, and further developed a better method for predicting individual differences in general intelligence, thereby completing the present invention.

SUMMARY OF THE INVENTION

It is an object of the present invention to provide a method for measuring neurometric IQ to measure human intelligence.

To achieve the above object, in one aspect, the present invention provides a system for measuring human neurometric IQ (nIQ), comprising: a unit for acquiring MRI and fMRI; a unit for processing acquired images; a unit for extracting structural predictors; and a unit for measuring intelligence.

In another aspect, the present invention provides a method for measuring the neurometric IQ (nIQ) of subjects, the method comprising the steps of: (1) acquiring MRI and fMRI images for the brains of the subjects; (2) processing the images acquired in step (1); (3) extracting a structural predictor (structural IQ; sIQ) and a functional predictor (functional IQ; fIQ) for the cerebra of the subjects from the processed images; and using the structural predictor and the functional predictor to measure the intelligence of the subjects.

In the inventive method, said sIQ is determined according to the following equation 1 based on cortical gray matter thicknesses ($t_i$), measured in intelligence-related brain regions of interest by analyzing the three dimensional structure of anatomical brain MRI images using a CLASP (Constrained Laplacian-based Automated Segmentation with Proximities) algorithm (Kim, et al, (2005) Automated 3-D extraction and evaluation of the inner and outer cortical surfaces using a Laplacian map and partial volume effect classification., NeuroImage, 27(1), 210-221):

$$sIQ = \alpha + \sum_{i=1}^{n} (\beta_i + \gamma_i \cdot s) \cdot t_i \quad \text{[Equation 1]}$$

wherein s represents the sex of the subjects and has a value of 1 for males and a value of 0 for females, n is the number of intelligence-related brain regions of interest (ROI), and $\alpha$, $\beta$ and $\gamma$ are values obtained by performing the linear regression analysis of the cortical thickness information of the subjects using a commercially available statistical package (SPSS ver. 12) to the information of cortical thicknesses of the subjects.

Also, said fIQ is determined according to the following equation based on activation levels ($a_i$), measured in intelligence-related regions of interest by analyzing the brain activation levels of fMRI images using statistical analysis software SPM (Statistical parametric maps, The Wellcome Department of Cognitive Neurology, Institute of Neurology, Functional Imaging Laboratory, London, UK):

$$fIQ = \alpha + \sum_{i=1}^{n} (\beta_i + \gamma_i \cdot s) \cdot a_i \quad \text{[Equation 2]}$$

wherein s represents the sex of the subjects and has a value of 1 for males and a value of 0 for females, n is the number of intelligence-related brain regions of interest (ROI), and $\alpha$, $\beta$ and $\gamma$ are values obtained by performing the linear regression analysis of the activation level data of the subjects using a commercially available statistical package (SPSS ver. 12).

In step (4), the following equation 3 is used to measure the intelligence of the subjects:

$$nIQ = \beta_1 \cdot sIQ + \beta_2 \cdot fIQ + \alpha \quad \text{[Equation 3]}$$

wherein nIQ is neurometric IQ, sIQ is structural IQ, fIQ is functional IQ, and $\alpha$, $\beta 1$ and $\beta 2$ are values obtained by performing the linear regression analysis of the sIQ and fIQ data of the subjects using a commercially available statistical analysis package (SPSS ver. 12).

The inventive neurometric model integrating structural and functional measures of the brain is highly useful as a new, neuroscientific methodology for measuring human intelligence.

DESCRIPTION OF DRAWINGS

FIG. 2A shows correlations between cortical gray matter thickness and Wechsler's Adult Intelligence Scale (WAIS) IQ. FIG. 2B shows the correlations between cortical activation during reasoning tasks and WAIS IQ. FIGS. 2C and 2D show the left dominance of correlation between cortical thickness and the cognitive ability. FIGS. 2E and 2F show the bilateral dominance of correlation between cortical activation and cognitive ability.

In FIG. 3, radar graphs show the simple correlation of each ROI's cortical thickness (A) or peak t score (C) with the three factors of intelligence: general (g, gray line), crystallized (gC, red line) and fluid intelligence (gF, blue line). Bar graphs display multiple correlations of all structural (B) or functional (D) ROI values with each factor of intelligence.

FIG. 4 shows gender differences in the pattern of intelligence-related regions. Each map shows correlations of cortical gray matter thickness to WAIS Verbal IQ and to Performance IQ. The left and right panels display the correlation data for men (n=89), and women (n=75), respectively. The color bar indicates absolute values of correlation coefficients.

FIGS. 5A and 5B show multiple linear regression models using structural predictors (cortical thickness of structural ROIs and brain volume), or functional predictors (cortical activation level of functional ROIs), and gender-predictor interaction terms. The scatter plots and linear regression lines show correlations of sIQ, or fIQ, with WAIS IQ. FIG. 5C shows a schematic model of neurometric IQ (nIQ) and the predictability estimate.

DESCRIPTION OF THE PREFERRED EMBODIMENTS

Hereinafter, the present invention will be described in further detail with reference to the following examples. It is to be understood, however, that these examples are illustrative only, and the scope of the present invention is not limited thereto.

As shown in FIGS. 1 to 6, the present invention provides a method for measuring human neurometric IQ (nIQ). Also, the present invention provides a system for measuring nIQ, comprising: a unit for acquiring MRI and fMRI; a unit for processing measured images; a unit for extracting structural predictors; and a unit for measuring intelligence.

The method for measuring nIQ comprises acquiring MRI and fMRI images for subjects, processing the measured images, and measuring predictors from the processed images to measure the nIQ of the subject.

In order to establish the inventive method for measuring nIQ and to prove that the inventive method for measuring nIQ has a statistically significant correlation with the prior conventional method for measuring IQ, the present inventors have conducted the following studies.

1. Selection of Subjects

Protocols were approved by institutional review boards (Seoul National University, Catholic University of Korea); written informed consent was obtained from the participants. 469 volunteers were recruited through advertisements and they were screened to cover the entire range of intelligence except mental disability. Finally, 225 healthy volunteers were retained with a wide distribution of WAIS full-scale IQ ($81 \leq IQ \leq 150$): 122 males/103 females, mean (SD) age=20.9 (2.9) years, IQ=118 (15). 164 and 109 subjects were scanned for anatomical and functional MRI data respectively, and forty eight subjects among them contributed for both structural and functional samples. Data from 33 subjects (functional sample) have been reported previously (Lee, K. H., Choi, Y. Y., Gray, J. R., Cho, S. H., Chae, J. H., Lee, S., et al. (2006). Neural correlates of superior intelligence: stronger recruitment of posterior parietal cortex. NeuroImage, 29(2), 578-586). For the structural sample, subjects were scanned at the Neuroscience Research Institute (NRI, Gachon University, Korea) or the Korea Advanced Institute of Science and Technology (KAIST, Korea). The two samples of subjects had no significant difference in WAIS IQ and RAPM score [$t(162)<0.24$, $P>0.8$] and gender ratio [$\chi^2=1.10$, $P>0.2$]. Moreover, the correlations of WAIS IQ and cortical thickness at each surface point were not significantly different between the NRI and KAIST samples ($P>0.001$ uncorrected; particularly in the ROIs, $P>0.01$ uncorrected) based on the results from Fisher's z transformation analyses.

2. Prior Conventional Psychometric Tests

All participants underwent both the Raven's Advanced Progressive Matrices Set II (RAPM) test and the Wechsler Adult Intelligence Scale-Revised (WAIS, Korean version) test. In the present invention, the score sums of the Information, Comprehension, Vocabulary, and Similarities subtests and of the Block Design, Object Assembly, and Picture Completion subtests were used as the scores of Verbal Comprehension (or gC) and of Perceptual Organization (or gF), respectively.

3. Anatomical MRI Acquisition

In the case of the NRI sample of subjects, contiguous 0.9 mm axial, three dimensional multi-planar rapidly acquired gradient echo (MPRAGE) images were acquired with a 1.5T MR scanner (Magnetom Avanto, Siemens) using the parameters: TR=1160 ms, TE=4.3 ms, flip angle=15°, field of view (FOV)=224 mm, matrix=512 by 512, number of slices=192, and averages=2. For the KAIST sample, 3D MPRAGE images were obtained with a 3T MR scanner (Forte, Isol Technology) using the parameters: TR=10 ms, TE=5.7 ms, flip angle=10°, FOV=220 mm, matrix=256 by 256, number of slices=128, and slice thickness=1.5 mm.

4. Image Processing

In order to measure the cortical thickness, several preprocessing algorithms were required. First, intensity non-uniformity in the raw MR images resulting from magnetic field inhomogeneity needed correction, so that the corrected volumes could be properly classified into gray matter (GM), white matter (WM) and cerebro-spinal fluid (CSF) (Sled, J. G., Zijdenbos, A. P., & Evans, A. C. (1998). A nonparametric method for automatic correction of intensity nonuniformity in MRI data. IEEE Trans Med Imaging, 17(1), 87-97). After comparing local histograms of image intensity in different spatial locations, the shift in the intensity histogram due to RF inhomogeneity was identified and corrected. Second, automatic registration to a stereotaxic space was performed using the intensity-corrected image to spatially normalize the brains (Collins, D. L., Neelin, P., Peters, T. M., & Evans, A. C. (1994). Automatic 3D intersubject registration of MR volumetric data in standardized Talairach space. J Comput Assist Tomogr, 18(2), 192-205; Talairach, J., & Tournoux, P. (1988). Co-planar stereotaxic atlas of the human brain: 3-dimensional proportional system. Stuttgart: Thieme). This method linearly transforms an MRI by using gradient descent at multiple scales to maximize the correlation between the individual volume intensity and an average volume intensity constructed from a large number of previously aligned brains. Third, a 3D stereotaxic brain mask was used to remove extracerebral voxels. The tissue classification is also required to reconstruct cortical surfaces. The discrete classification employs an Intensity-Normalized Stereotaxic Environment for Classification of Tissues (INSECT) (Zijdenbos, A. P., Forghani, R., & Evans, A. C. (2002). Automatic "pipeline" analysis of 3-D MRI data for clinical trials: application to multiple sclerosis. IEEE Trans Med Imaging, 21(10), 1280-1291). To reveal the buried CSF in sulci, the present inventors utilized the probabilistic classification, which provided combined information on GM and CSF. The probabilistic CSF voxels outlined the sulcal walls.

5. Cortical Thickness

Thickness measurement requires specific algorithms to reconstruct inner and outer cortical surfaces (MacDonald, D., Kabani, N., Avis, D., & Evans, A. C. (2000). Automated 3-D extraction of inner and outer surfaces of cerebral cortex from MRI. NeuroImage, 12(3), 340-356). These surfaces are automatically reconstructed by the Constrained Laplacian-based Automated Segmentation with Proximities (CLASP) algorithm (Kim, J. S., Singh, V., Lee, J. K., Lerch, J., Ad-Dab'bagh, Y., MacDonald, D., et al. (2005). Automated 3-D extraction and evaluation of the inner and outer cortical surfaces using a Laplacian map and partial volume effect classification. NeuroImage, 27(1), 210-221). CLASP extracts the inner cortical surface by deforming a sphere polygon model to the boundary between GM and WM. The number of triangles of the polygon model is hierarchically refined from 320 to 80920. Then, the outer cortical surface is expanded from the inner surface to the boundary between GM and CSF along a Laplacian map, which smoothly increases potential surfaces between WM and CSF. A CSF fraction image is skeletonized to determine the boundary of the outer cortex in buried sulci (Ma, C.-M., & Wan, S.-Y. (2001). A medial-surface oriented 3-d two-subfield thinning algorithm. Pattern Recogn. Lett., 22, 1439-1446). The present inventors constructed hemispheric cortical surface models, each of which consisted of 81,920 polygons forming high-resolution meshes of discrete triangular elements. Since the cortical surface models were extracted from MR volumes transformed into stereotaxic space, to measure cortical thickness in native space, the present inventors applied an inverse transformation matrix to cortical surfaces and reconstructed them in native space. Inner and outer surfaces have the same vertex number (40962) and each vertex between surfaces is related. Thus, the cortical thickness is easily measured as the distance between related vertices in native space. In order to reduce variations caused by distinct characteristics of the particular scanner, the thickness was standardized at each cortical surface location only within the respective NRI and KAIST samples.

6. Statistical Analysis

In the present invention, an available package (SPSS ver. 12) was used for statistical analysis. The previous section showed that every vertex has the thickness information on the cortical surface. To compare the thickness across subjects, the thickness information is spatially normalized. In the CLASP algorithm, the cortical surfaces start from a spherical polygon model. The vertices are easily transformed to the spherical model. Vertices are also nonlinearly registered to an average template on the sphere. A highly flexible deformation, in two dimensions, of a template cortex to an individual is used for the cortical surface registration (Robbins, S. M. (2003). Anatomical standardization of the human brain in Euclidean 3-space and on the cortical 2-manifold. Unpublished PhD thesis, McGill University, Montreal). This algorithm provides transformation to match crowns of gyri between subjects using a geodesic distance map. With the transformation, thickness information on the vertices is transformed to a template. Then, diffusion smoothing, which generalizes Gaussian kernel smoothing, with 30 mm FWHM (full width half maximum) is used to increase the signal to noise ratio (Chung, M., Worsley, K., Paus, T, Robbins, S., Evans, A., Taylor, J., et al. (2002). Tensor-based surface morphometry. Madison, Wis.: University of Wisconsin). Statistical parametric maps of cortical correlates of intelligence are constructed by using Pearson correlation. The distribution of thickness across the whole brain is assessed initially on a vertex-by-vertex basis.

As a result, the cortical gray matter thickness ($t_i$) of brain regions of interest, which is an important factor for the measurement of sIQ, was determined.

7. fMRI Experiments fMRI is a technique for imaging the change in blood oxygen level dependant signal (BOLD signal) with brain activation levels. The intensity of the BOLD signal is in linear correlation with the change in brain blood flow and can be used to determine brain activation levels. To identify functional correlates of intelligence, the present inventors used the two behavioral tasks (the simple g-task and the complex g-task) that were previously developed for fMRI. That is, the present inventors comparatively analyzed brain activation when performing cognitive tasks having different difficulties (Lee, K. H., Choi, Y. Y., Gray, J. R., Cho, S. H., Chae, J. H., Lee, S., et al. (2006). Neural correlates of superior intelligence: stronger recruitment of posterior parietal cortex. NeuroImage, 29(2), 578-586).

As a result, activation levels ($a_i$) in brain regions, which are an important factor for fIQ measurement, were determined.

8. Results

First, to find common neural ground of intelligence in terms of brain anatomy and physiology, the present inventors constructed statistical maps of cortical gray matter thickness and blood oxygenation level dependent (BOLD) signal changes relevant to IQ. First, structural MR images of 164 subjects were processed to determine cortical gray matter thickness at each brain surface point matched across individuals. Simple regression was used to identify brain regions whose thicknesses predict WAIS IQ (FIG. 2A). In FIG. 2A, the color bar indicates statistical significance of the correlations (right side, positive correlation; left side, negative correlation), and lines point to the five regions with a high statistical significance (P<0.001 uncorrected): anterior temporal (ATC), anterior parietal (APC), opercular temporal (OTC), inferior temporal (ITC), and medial temporal (MTC) cortices. The left hemisphere manifested significant correlations in anterior temporal (ATC), opercular temporal (TOC), inferior temporal (ITC), and anterior parietal cortices (APC), while the right hemisphere showed significant correlations in medial temporal cortex (MTC) (P<0.001 uncorrected). When the left and right area sizes of the correlations were compared on the basis of statistical significance (P<0.001 uncorrected), the left hemisphere had more extensive areas than the right one (FIG. 2C) and, also on a lobar level, all the left sides of the frontal, temporal, insular, and parietal cortices were larger in correlational area size than the right sides (FIG. 2D). In FIGS. 2C and 2D, the sizes of the cortical areas were defined using a statistical significance of the correlation (P<0.001 uncorrected). The abbreviations are as follows: Fro, frontal lobe; Tem, temporal lobe; Ins, Insular lobe; Par, parietal lobe; Occ, occipital lobe; L, left; R, right. Second, the present inventors similarly performed a simple regression analysis to predict WAIS IQ by local activation level for 109 subjects who underwent functional MR scans when performing g-loaded reasoning tasks (see Method), and found significant positive correlations throughout the brain (P<0.001 uncorrected; FIG. 1B), particularly in the bilateral posterior parietal (PPC), bilateral prefrontal (PFC), and anterior cingulate cortices (ACC) (see FIG. 2B). In FIG. 2B, the map depicts the results of a simple regression analysis with IQ score as a covariate. The color bar indicates statistical significance of the correlations. Lines point to the five regions with a high statistical significance (P<0.001, uncorrected): anterior cingulate (ACC), bilateral prefrontal (PFC), and bilateral posterior parietal (PPC) cortices. In contrast to the structural correlates, when the left and right volumes of the correlations were compared, the functional correlates showed no left lateral dominance, rather a slight right lateral dominance in the full hemisphere (FIG. 2E) and all the lobes except the prefrontal lobe (FIG. 2F). In FIGS. 2E and 2F, the volume sizes of the activations was defined using a statistical significance (P<0.001 uncorrected). The abbreviations are as follows: Fro, frontal lobe; Tem, temporal lobe; Ins, Insular lobe; Par, parietal lobe; Occ, occipital lobe; L, left; R, right.

Figure 1:
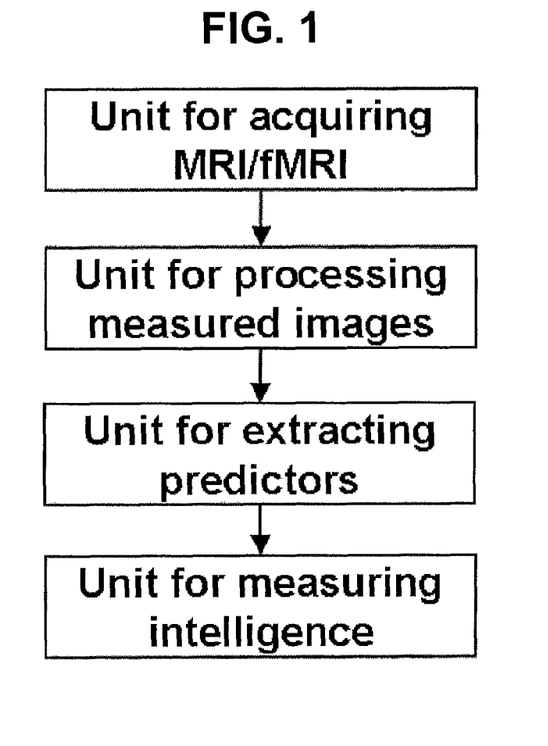
FIG. 1 shows the structure of the inventive system for measuring human neurometric IQ (nIQ).
Figure 2:
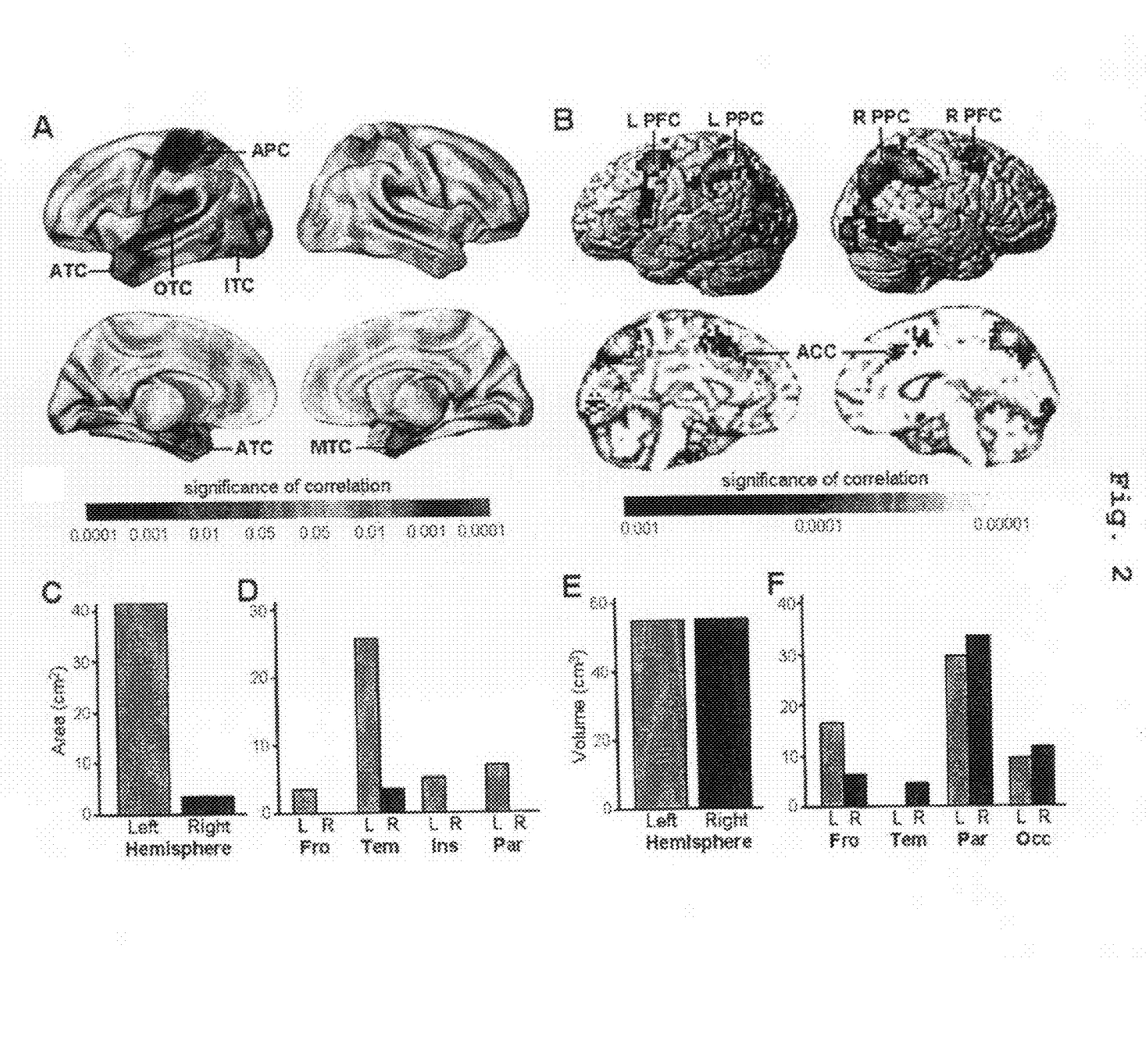
FIG. 2 shows the structural and functional correlates of intelligence and their laterality. Specifically.
Figure 3:
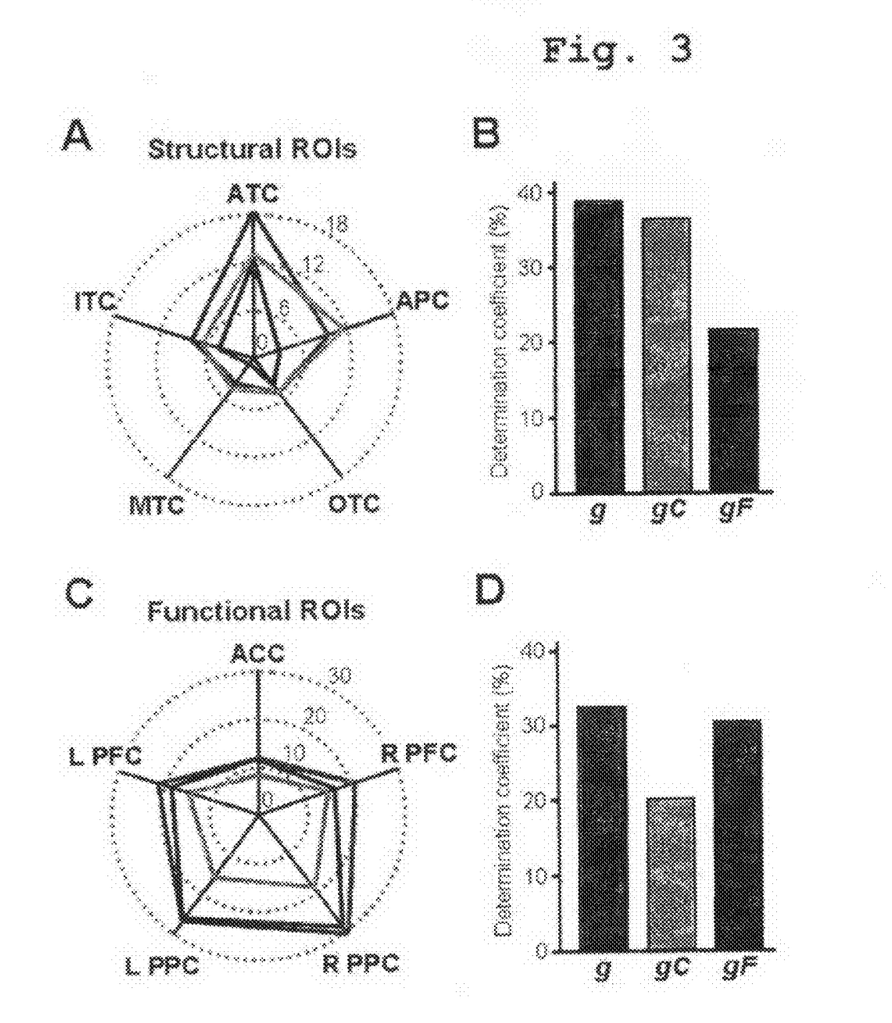
FIG. 3 shows the contrast between structural and functional ROIs in relationship to major components of intelligence.
Figure 4:
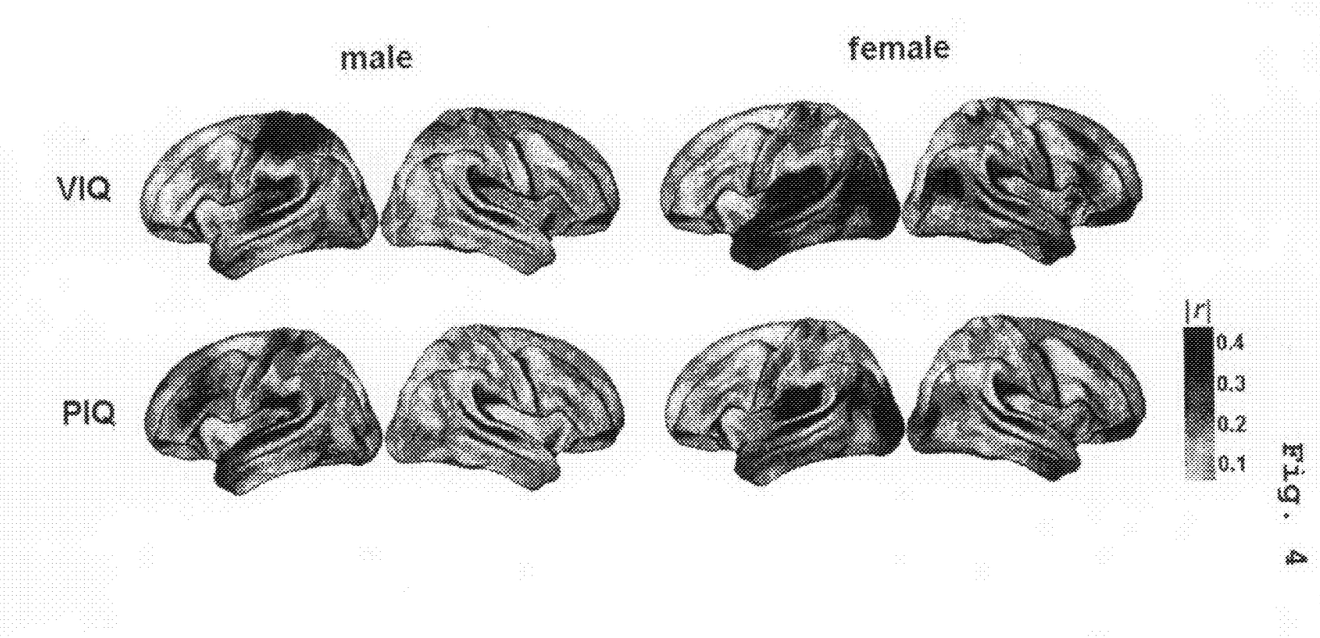
Figure 5:
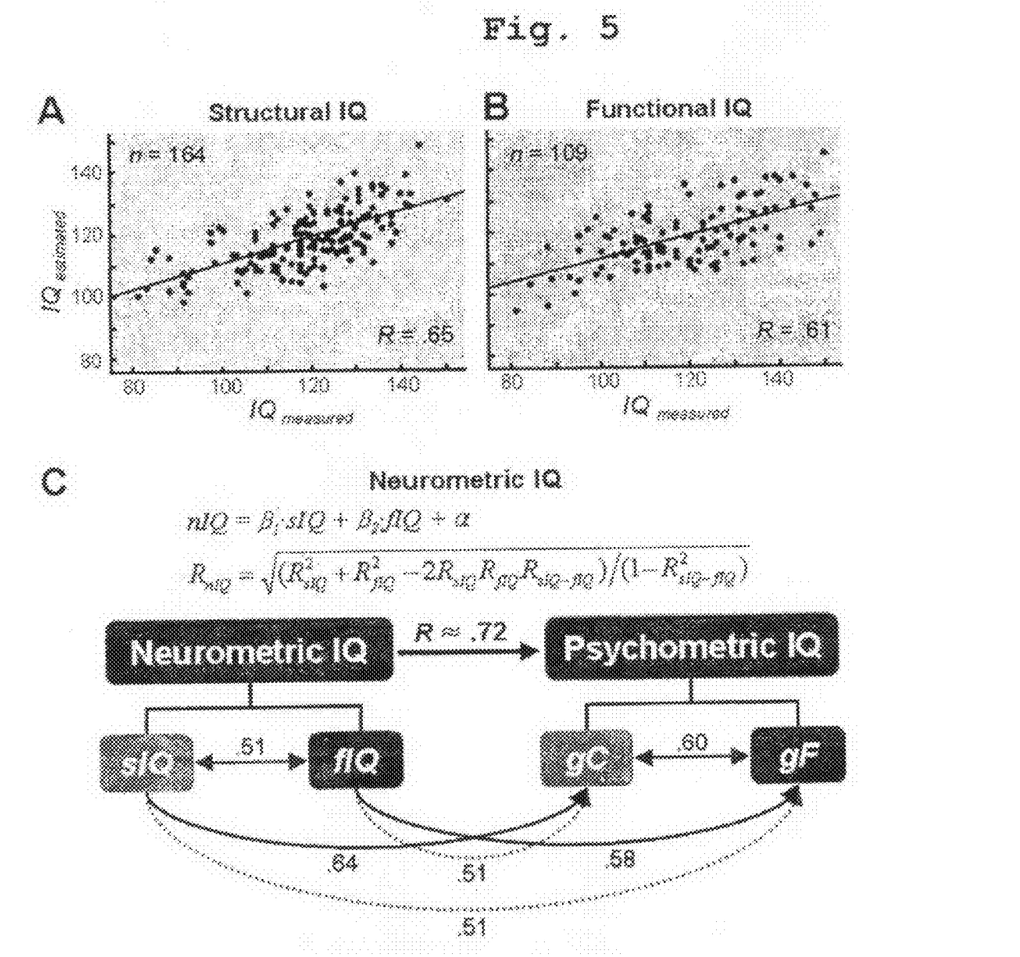
FIG. 5 shows predictability of structural IQ, functional IQ, and neurometric IQ. Specifically.

The contrasting laterality and non-overlapping localization of the structural and functional correlates of intelligence suggests that the two types of correlates may reflect the different dimensions of general intelligence. Especially, considering that the left brain is dominant for language processing, the left laterality of the structural correlates suggests that the structural correlates may be tightly associated with cognitive abilities relevant to verbal information processing, namely crystallized intelligence. To address this issue, the present inventors analyzed the structural and functional correlates' relationships to the three major components of intelligence: general (g), crystallized (gC), and fluid (gF) intelligence. Structural and functional regions of interest (ROIs) first were determined by using the correlated areas with a statistical significance (P<0.001). Simple and multiple regression analyses were used to find which components of intelligence (g, gC and gF) are predicted well by each ROI's value (peak thickness or peak t score). Intriguingly, although both structural and functional ROIs' values generally were most correlated with g, structural ROIs' values tended to predict well gC rather than gF and, for functional ROIs, vice versa (FIGS. 3A and 3C). Notably, when all five ROI values were used as predictive variables, the multiple regression analysis showed that the five structural ROI values predicted gC ($R^2$=32%) better than gF ($R^2$=15%; FIG. 3B), while the five functional ROI values predicted gF ($R^2$=24%) better than gC ($R^2$=20%; FIG. 3D). The multiple regression analysis provided strong links between gray matter and gC. In FIG. 3, each bar or line indicates the amount of explained variance ($R^2$) on individual performance on the intelligence scores. g, principal component of all WAIS subtests and RAPM (Raven's Advanced Progressive Matrices Set II); gC, principal component of WAIS Verbal Comprehension subtests; gF, principal component of WAIS Perceptual Organization subtests and RAPM. The abbreviations are as follows: ATC, anterior temporal cortex; APC, anterior parietal cortex; OTC, opercular temporal cortex; ITC, inferior temporal cortex; MTC, medial temporal cortex; ACC, anterior cingulate cortex; L, left; R right; PFC, prefrontal cortex; PPC; posterior parietal cortex.

To further probe the structural correlates' relationship to verbal modality, the present inventors performed correlational analysis at a subtest level using all verbal and performance scores of WAIS. As shown in Table 1 below, in all ROIs, verbal IQ revealed stronger associations with cortical thickness than performance IQ. Moreover, APC, LOC, and MTC did not reach a statistical significance (P=0.01) in performance IQ. Also at a subtest level, when verbal and performance scores were compared in each ROI, verbal scores tended to show more significant correlations with cortical thickness than performance scores. In addition, the present inventors constructed male and female maps of verbal IQ and performance IQ separately (FIG. 4) for excluding possible gender confound because gender has an effect on brain structure (Goldstein, J. M., Seidman, L. J., Horton, N. J., Makris, N., Kennedy, D. N., Caviness, V. S., Jr., et al. (2001). Normal sexual dimorphism of the adult human brain assessed by in vivo magnetic resonance imaging. Cereb Cortex, 11(6), 490-497; Im, K., Lee, J. M., Lee, J., Shin, Y. W., Kim, I. Y. Kwon, J. S. et al. (2006). Gender difference analysis of cortical thickness in healthy young adults with surface-based methods. Neuroimage, 31(1), 31-38). The gender-specific maps of verbal and performance IQ showed an intriguing pattern where the temporal cortices showed a strong correlation to verbal IQ in women, while the parietal cortices showed a strong correlation to verbal IQ in men. These results suggest that gender may be a factor that, to some extent, accounts for the variability of the brain structures.

TABLE 1

Comparison between correlation coefficients of regional thickness to Verbal and to Performance scores

| Test | Correlation coefficient (r) | | | | |
|---|---|---|---|---|---|
| | ATC | ITC | OTC | MTC | APC |
| Verbal IQ | 0.43** | 0.30** | 0.24* | 0.24* | −0.33** |
| Information | 0.36** | 0.23* | 0.21* | 0.16 | −0.31** |
| Comprehension | 0.37** | 0.23* | 0.22* | 0.20 | −0.22* |
| Vocabulary | 0.31** | 0.15 | 0.19 | 0.23* | −0.30** |
| Arithmetic | 0.41** | 0.30** | 0.13 | 0.18 | −0.30** |
| Similarities | 0.22* | 0.28** | 0.15 | 0.13 | −0.33** |
| Digit span | 0.28** | 0.20* | 0.16 | 0.15 | −0.16 |
| Performance IQ | 0.36** | 0.20* | 0.20* | 0.15 | −0.18 |
| Picture completion | 0.15 | 0.09 | 0.16 | 0.06 | −0.08 |
| Picture arrangement | 0.29** | 0.14 | 0.08 | 0.11 | −0.08 |
| Digit symbol | 0.14 | 0.10 | 0.07 | 0.08 | −0.18 |
| Block design | 0.29** | 0.22* | 0.19 | 0.08 | −0.16 |
| Object assembly | 0.24* | 0.15 | 0.06 | 0.06 | −0.11 |

Each value is a Pearson's correlation coefficient between the cortical thickness of the intelligence-related regions and the scores of WAIS Verbal and Performance tests. ATC, anterior temporal cortex; APC, anterior parietal cortex; OTC, opercular temporal cortex; ITC, inferior temporal cortex; MTC, medial temporal cortex.
*P < 0.01;
**P < 0.001.

The aforementioned results hinted that structural and functional information of the brain may provide different perspectives on intelligence, and further suggest that the combined information on the structure and function of the brain may predict psychometric IQ well. To inquire the possibility that psychometric IQ can be estimated by the intelligence-related measures of the brain ("neurometric" IQ), the present inventors chose to estimate the predictability of neurometric IQ (nIQ). Because anatomical and functional data were acquired from different subject samples and there were only 48 subjects having both anatomical and functional images, the present inventors first estimated the extents to which the structural (sIQ) and functional (fIQ) measures foretell psychometric IQ, respectively and then calculated the predictability of nIQ using the formula for multiple correlation coefficient (see the second equation in FIG. 5C) when sIQ and fIQ were assumed as the two predictive variables (see the first equation in FIG. 5C). For these analyses, the present inventors added cerebral volume to structural predictors to increase predictability since brain volume is known to be correlated with IQ (Posthuma, D., de Geus, E. J. C., Baare, W. F. C., Hulshoff Pal, H. E., Kahn, R. S., & Boomsma, D. I. (2002). The association between brain volume and intelligence is of genetic origin. Nat. Neurosci., 5(2), 83-84; Witelson, S. F., Beresh, H., & Kigar, D. L. (2006). Intelligence and brain size in 100 postmortem brains: sex, lateralization and age factors. Brain, 129, 386-398)

The present inventors first constructed multiple linear regression models using only strlicLural predictors (cortical thickness of structural ROIs and brain volume), or functional predictors (cortical activation level of functional ROIs), and gender-predictor interaction terms. The scatter plots and linear regression lines showed the correlation of sIQ (r=0.64; FIG. 5A), or fIQ (r=0.61; FIG. 5B), with WAIS IQ. Although the predictabilities (r) of sIQ and fIQ were about 0.6, the predictability of the regression model using both sIQ and fIQ as predictors was improved as R=0.72 (FIG. 5C). Additionally, the schematic model in FIG. 50 illustrated that the neurometric IQ model was organized to be parallel with the constitution of psychometric IQ: As psychometric IQ has the two components of intelligence called gC and gF, the neurometric IQ model contained the two parts, sIQ and fIQ that had a strong link to gC and to gF, respectively. In FIG. 5C, When a linear regression model using sIQ and fIQ as predictors (the first equation) is applied, the predictability of nIQ can be estimated using the second equation, where the correlation coefficient between sIQ and fIQ (RsIQ-fIQ) is calculated in the sample having both structural and functional data (n=48). The first equation expresses a linear regression model for nIQ by combining sIQ and fIQ. $\beta 1$, $\beta 2$ and $\alpha$ are fitting parameters. The second equation was developed to explain relationship between nIQ and psychometric IQ (pIQ). Ra is a correlation coefficient between variable "a" and WAIS IQ. Each value on the arrowed line is the correlation coefficient between the connected cognitive dimensions. Weak and strong relationships between the subdimensional scales were shown in dotted line and solid line, respectively.

Figure 6:
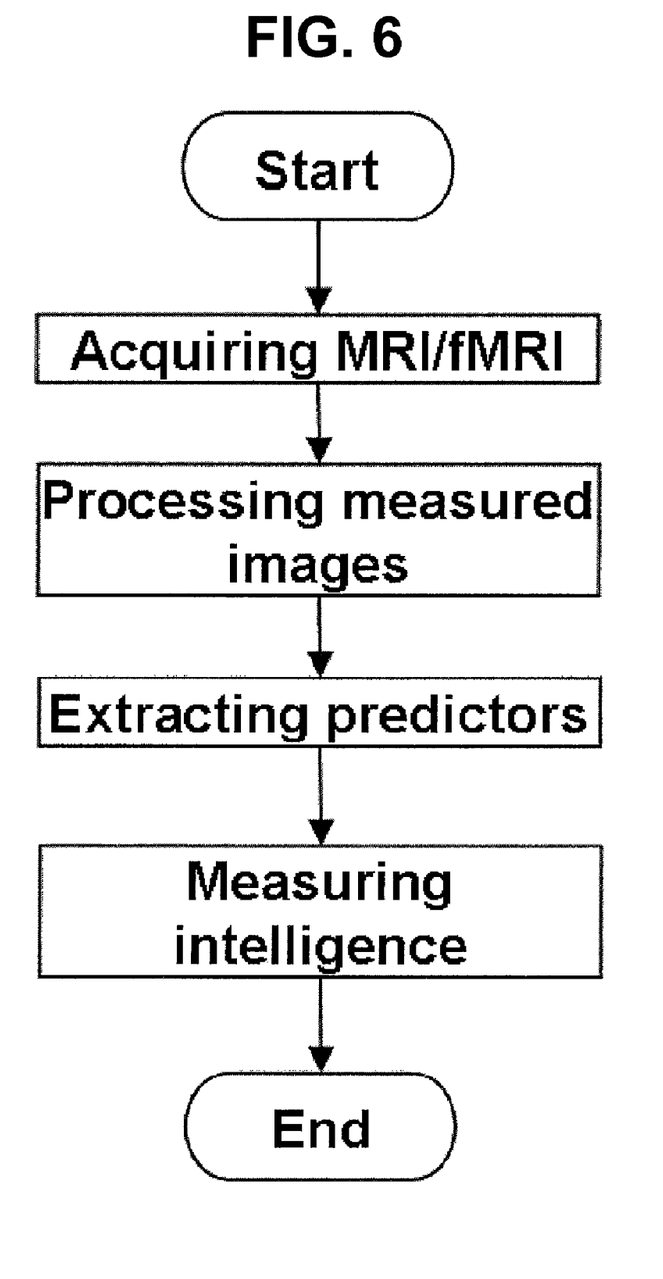
FIG. 6 shows a flow chart of the inventive method for measuring human neurometric IQ (nIQ).

The method for measuring nIQ according to the present invention is shown in FIG. 6.

9. Method for Measuring nIQ

A method for measuring nIQ for subjects (n=15) will now be described with reference to the flow chart of FIG. 6. MRI and fMRI images were acquired from the subjects, and the measured images were processed. In the processing step, cortical gray matter thicknesses ($t_i$) in brain regions of interest in (ROI) [ATC (t1), APC (t2), OTC (t3), MTC (t4), and ITC (t5)] were determined by analyzing the three-dimensional structure of the MRI images using the CLASP algorithm, and $\alpha$, $\beta$ and $\gamma$ were determined using SPSS (ver. 12). The results are shown in Table 2 below.

TABLE 2

Thickness information, α, β and γ for measurement of sIQ

| | Thickness (mm) | | | | | |
|---|---|---|---|---|---|---|
| Subject | ATC (t1) | ARC (t2) | OTC (t3) | MTC (t4) | ITC (t5) | WAIS IQ |
| 1 | 3.3973 | 3.0284 | 3.0795 | 3.6505 | 3.0779 | 81 |
| 2 | 3.5472 | 2.7697 | 3.3587 | 3.5223 | 3.3579 | 88 |
| 3 | 3.5360 | 3.0874 | 3.1505 | 3.5489 | 3.4823 | 93 |
| 4 | 3.8016 | 2.8780 | 3.3382 | 3.6214 | 3.6255 | 97 |
| 5 | 3.7832 | 3.0646 | 3.2731 | 3.9524 | 3.1609 | 105 |
| 6 | 3.7801 | 2.9581 | 3.3682 | 3.5327 | 3.2249 | 108 |
| 7 | 3.3342 | 2.8050 | 3.1301 | 3.1419 | 3.1461 | 113 |
| 8 | 3.8213 | 2.8505 | 3.3702 | 3.9210 | 3.2560 | 117 |
| 9 | 3.8817 | 3.1234 | 3.2663 | 3.6792 | 3.3297 | 122 |
| 10 | 3.7469 | 2.7438 | 3.4123 | 3.1262 | 3.4203 | 127 |
| 11 | 3.5629 | 2.3785 | 3.0868 | 3.3649 | 3.1556 | 131 |
| 12 | 3.9575 | 2.8174 | 3.5140 | 3.7757 | 3.4038 | 134 |
| 13 | 3.7681 | 2.8313 | 3.3822 | 3.8388 | 3.3457 | 137 |
| 14 | 3.6394 | 2.3826 | 3.3438 | 5.5450 | 3.1986 | 140 |
| 15 | 4.4467 | 2.7812 | 3.7359 | 4.1725 | 5.8156 | 143 |
| beta | 99.6398 | 0.9414 | −124.8373 | −42.3440 | −32.7557 | |
| gamma | 82.7929 | −113.4095 | −40.2608 | 32.7403 | 15.2224 | |
| alpha | | | | | | 404.6752 | sIQ was calculated by substituting the thickness, α, β and γ of Table 2 into the above equation 1.

Also, activation levels ($a_i$) in brain regions of interest (ROI) [ACC (a1), LPFC (a2), LPPC (a3), RPFC (a4), and RPPC (a5)] were determined by analyzing the fMRI images with SPM, and α, β and γ were calculated using SPSS (ver. 12). The results are shown in Table 3 below.

TABLE 3

Thickness information, α, β and γ for measurement of fIQ

| | Activation level | | | | | |
|---|---|---|---|---|---|---|
| Subject | ACC (a1) | LPFC (a2) | LPPC (a3) | RPFC (a4) | RPPC (a5) | WAIS IQ |
| 1 | 2.7085 | 2.8215 | 2.5165 | 1.9046 | 2.1041 | 81 |
| 2 | 7.2521 | 6.8693 | 5.2058 | 7.2541 | 7.1003 | 88 |
| 3 | 0.8535 | 2.1237 | 2.2300 | 1.0377 | 3.8223 | 93 |
| 4 | 6.0600 | 9.4847 | 8.5689 | 8.8851 | 7.8487 | 97 |
| 5 | 5.7802 | 4.7600 | 7.9985 | 5.2947 | 7.2680 | 105 |
| 6 | 1.6210 | 4.0212 | 5.1512 | 1.5848 | 6.4020 | 108 |
| 7 | 4.0608 | 5.9765 | 7.5389 | 4.3258 | 8.3258 | 113 |
| 8 | 6.8896 | 10.1790 | 11.4300 | 8.4357 | 9.3353 | 117 |
| 9 | 3.4636 | 3.9196 | 5.5628 | 2.2059 | 5.7121 | 122 |
| 10 | 5.8808 | 6.7124 | 9.4525 | 5.7221 | 11.0710 | 127 |
| 11 | 5.7813 | 7.8934 | 6.8647 | 4.6133 | 5.8107 | 131 |
| 12 | 7.9392 | 7.1404 | 7.1819 | 6.8002 | 7.5485 | 134 |
| 13 | 3.1627 | 6.3811 | 7.5189 | 4.6214 | 7.8052 | 137 |
| 14 | 5.2475 | 7.0462 | 6.8134 | 6.8143 | 7.3541 | 140 |
| 15 | 8.0830 | 11.4660 | 12.6420 | 7.3136 | 12.7440 | 143 |
| beta | 14.3825 | 5.9361 | −10.8812 | −11.6721 | 8.8032 | |
| gamma | −18.1314 | −7.7279 | 13.7184 | 15.1036 | −4.8209 | |
| alpha | | | | | | 79.9595 | fIQ was calculated by substituting the thickness, α, β and γ of Table 3 into the above equation 2.

α and β were determined from the above-calculated sIQ and fIQ values with SPSS (ver. 12), and substituted into the above equation 3, thus determining nIQ. The results are shown in Table 4 below.

TABLE 4 sIQ, fIQ and parameters α and β for measurement of nIQ

| Subject | sIQ | fIQ | WAIS IQ |
|---|---|---|---|
| 1 | 86.41 | 86.80 | 81 |
| 2 | 93.08 | 108.40 | 88 |
| 3 | 87.24 | 98.06 | 93 |
| 4 | 97.34 | 95.57 | 97 |

TABLE 4-continued sIQ, fIQ and parameters α and β for measurement of nIQ

| Subject | sIQ | fIQ | WAIS IQ |
|---|---|---|---|
| 5 | 105.01 | 106.50 | 105 |
| 6 | 108.41 | 108.95 | 108 |

TABLE 4-continued sIQ, fIQ and parameters α and β for measurement of nIQ

| Subject | sIQ | fIQ | WAIS IQ |
|---|---|---|---|
| 7 | 112.69 | 114.61 | 113 |
| 8 | 130.06 | 134.44 | 117 |
| 9 | 121.77 | 117.05 | 122 |
| 10 | 126.29 | 136.43 | 127 |
| 11 | 130.73 | 132.57 | 131 |
| 12 | 133.69 | 111.17 | 134 |
| 13 | 119.75 | 124.94 | 137 |
| 14 | 139.26 | 119.66 | 140 |
| 15 | 144.27 | 140.83 | 143 |
| beta | 0.9963 | 0.0052 | |
| alpha | | | −0.1728 |

As described above, the statistical significance between the inventive nIQ measurement method and the prior IQ measurement method was proven, and these results suggest that the neurometric model integrating structural and functional measures of the brain may introduce a new, neuroscientific methodology to measure human intelligence.

Also, the present invention can assist in the treatment of dementia disease, which at this time still cannot be diagnosed early, because, when cortical thicknesses in brain regions closely connected with the gC of a patient supposed to have dementia is significantly different from mean thickness in patients of the same age group as the dementia patient, the difference is not simply attributable to low intelligence, but rather may be attributable to lesions.

INDUSTRIAL APPLICABILITY

As described above, the neurometric IQ concept that uses the equations for structural IQ and functional IQ, derived according to the present invention, is useful for assessing individual differences in general cognitive ability.

What is claimed is:

1. A method for measuring neurometric IQ (nIQ) of a subject, the method comprising the steps of:
   (1) acquiring MRI and fMRI images for a brain of a subject;
   (2) processing the images measured in step (1);
   (3) determining structural predictors (structural IQ; sIQ) by using cortical thickness information and functional predictors (functional IQ; fIQ) by using activation level data for cerebra of the subject from the processed images;
   wherein said sIQ is determined according to Equation 1 below:

$$sIQ = \alpha + \sum_{i=1}^{n} (\beta_i + \gamma_i \cdot s) \cdot t_i \qquad \text{[Equation 1]}$$

wherein $t_i$ is cortical gray matter thickness, s represents the sex of the subject and has a value of 1 in case where the subject is male and a value of 0 in case where the subject is female, n is the number of intelligence-related brain regions of interest (ROI), and α, β, and γ are values obtained by performing linear regression analysis of cortical thickness information of the subject and wherein said fIQ is determined according to Equation 2 below:

$$fIQ = \alpha + \sum_{i=1}^{n} (\beta_i + \gamma_i \cdot s) \cdot a_i \qquad \text{[Equation 2]}$$

wherein $a_i$ is brain activation level of the subject, s represents the sex of the subject and has a value of 1 in case where the subject is male and a value of 0 in case where the subject is female, n is the number of intelligence-related brain regions of interest (ROI), and α, β, and γ are values obtained by performing linear regression analysis of activation level data of the subject;

(4) measuring neurometric IQ (nIQ) of the subject by using the determined structural predictors and the functional predictors wherein said neurometric IQ of the subject is measured in step (4) according to Equation 3 below:

$$nIQ = \beta_1 \cdot sIQ + \beta_2 \cdot fIQ + \alpha \qquad \text{[Equation 3]}$$

wherein nIQ is neurometric IQ, sIQ is structural IQ, fIQ is functional IQ, and α, β1, and β2 are values obtained by performing linear regression analysis of sIQ and fIQ data of the subject.

2. A system for measuring neurometric IQ (nIQ) of a subject, the system comprising:
   (a) a unit for acquiring MRI and fMRI images for a brain of a subject;
   (b) a unit for processing the images acquired by the unit (a);
   (c) a unit for determining structural predictors (structural IQ; sIQ) by using cortical thickness information and functional predictors (functional IQ; fIQ) by using activation level data for cerebra of the subject from the images processed by the unit (b)
   wherein said sIQ is determined according to Equation 1 below:

$$sIQ = \alpha + \sum_{i=1}^{n} (\beta_i + \gamma_i \cdot s) \cdot t_i \qquad \text{[Equation 1]}$$

wherein $t_i$ is cortical gray matter thickness, s represents the sex of the subject and has a value of 1 in case where the subject is male and a value of 0 in case where the subject is female, n is the number of intelligence-related brain regions of interest (ROI), and α, β, and γ are values obtained by performing linear regression analysis of cortical thickness information of the subject and wherein said fIQ is determined according to Equation 2 below:

$$fIQ = \alpha + \sum_{i=1}^{n} (\beta_i + \gamma_i \cdot s) \cdot a_i \qquad \text{[Equation 2]}$$

wherein $a_i$ is brain activation level of the subject, s represents the sex of the subject and has a value of 1 in case where the subject is male and a value of 0 in case where the subject is female, n is the number of intelligence-related brain regions of interest (ROI), and α, β, and γ are values obtained by performing linear regression analysis of activation level data of the subject; and (d) a unit for measuring neurometric IQ (nIQ) of the subject by using the structural predictors and the functional predictors determined by the unit (c) wherein said neurometric IQ of the subject is measured according to Equation 3 below:

$$nIQ = \beta_1 \cdot sIQ + \beta_2 \cdot fIQ + \alpha \qquad \text{[Equation 3]}$$

wherein nIQ is neurometric IQ, sIQ is structural IQ, fIQ is functional IQ, and $\alpha$, $\beta 1$, and $\gamma 2$ are values obtained by performing linear regression analysis of sIQ and fIQ data of the subject.

* * * * *